(12) United States Patent
Choai

(10) Patent No.: US 12,727,978 B2
(45) Date of Patent: Sep. 8, 2026

(54) **EXPANDABLE DENTAL FLOSS HAVING FILAMENTS INFUSED WITH *NIGELLA SATIVA* AND ANTISEPTIC AND METHOD OF FORMING**

(71) Applicant: BIOM, LLC, Sheridan, WY (US)

(72) Inventor: Ilon Choai, Sheridan, WY (US)

(73) Assignee: BIOM, LLC, Sheridan, WY (US)

( * ) Notice: Subject to any disclaimer, the term of this patent is extended or adjusted under 35 U.S.C. 154(b) by 14 days.

(21) Appl. No.: 18/916,821

(22) Filed: Oct. 16, 2024

(65) Prior Publication Data

US 2025/0177104 A1 Jun. 5, 2025

Related U.S. Application Data

(60) Provisional application No. 63/606,121, filed on Dec. 5, 2023.

(51) Int. Cl.
*A61C 15/04* (2006.01)
*A61K 8/9789* (2017.01)
*A61Q 11/00* (2006.01)

(52) U.S. Cl.
CPC .......... *A61C 15/041* (2013.01); *A61K 8/9789* (2017.08); *A61Q 11/00* (2013.01)

(58) Field of Classification Search
CPC ....... A61C 15/00; A61C 15/04; A61C 15/041; A61K 8/9789; A61Q 11/00
See application file for complete search history.

(56) References Cited

U.S. PATENT DOCUMENTS

| | | | | |
|---|---|---|---|---|
| 7,174,903 B2 * | 2/2007 | Longoni | .............. | A61C 15/041 132/321 |
| 8,100,261 B2 | 1/2012 | Longoni et al. | | |
| 12,065,766 B2 | 8/2024 | De La Rue | | |
| 2011/0297181 A1 * | 12/2011 | Soloway | ............. | A61C 15/041 87/8 |
| 2016/0262352 A1 * | 9/2016 | Matsumoto | ............ | A23K 40/25 |
| 2018/0338903 A1 | 11/2018 | Ibrahim | | |

OTHER PUBLICATIONS

Genovesi et al., "Experimentation in Plaque Control in the Interproximal Spaces Using Dental Floss," Trial Report; Genoa University, Medicine & Surgery Faculty, Preventive Dentistry Department; Jan. 2004; pp. 1-5.

Mekhemar et al., "*Nigella sativa* and Thymoquinone: A Natural Blessing for Periodontal Therapy," Antioxidants; vol. 9, Issue 12; 1260; Dec. 11, 2020; pp. 1-20.

* cited by examiner

*Primary Examiner* — Rachel R Steitz
(74) *Attorney, Agent, or Firm* — ALLEN, DYER, DOPPELT + GILCHRIST, P.A.

(57) ABSTRACT

An expandable dental floss includes a plurality of texturized threads twisted together forming a floss element. Each texturized thread includes a plurality of pre-oriented yarn (POY) filaments. A first set of texturized threads has the plurality of POY filaments infused with *Nigella sativa*. A second set of the texturized threads has the plurality of POY filaments infused with an antiseptic composition.

11 Claims, 3 Drawing Sheets

EXPANDABLE DENTAL FLOSS HAVING FILAMENTS INFUSED WITH *NIGELLA SATIVA* AND ANTISEPTIC AND METHOD OF FORMING

PRIORITY APPLICATION(S)

This application is based upon provisional Application No. 63/606,121 filed Dec. 5, 2023, the disclosure which is hereby incorporated by reference in its entirety.

FIELD OF THE INVENTION

The present invention relates to the field of oral healthcare products, and more particularly, this invention relates to dental floss.

BACKGROUND OF THE INVENTION

Bacterial plaque may be formed as a biofilm from bacteria and food residue remaining on teeth that causes dental decay and gum disease. Plaque needs to be removed daily because it grows and hardens over time forming tartar, ultimately injuring not only the tooth, but the gums and creating periodontal disease. This danger is lessened when flossing becomes a daily routine.

Dental floss is a thin, textile filament or plurality of coupled filaments that help remove plaque to prevent the build-up of tartar, which may cause gingivitis or other inflammation of the gums. If this occurs, pockets where the teeth are positioned may become infected and destroy the bone that supports the tooth. Flossing disturbs the bacteria before it can create plaque and cause gum and bone disease.

Dental floss is commonly made from nylon, Teflon (PTFE), polyamide, or polyester filaments. Many different filaments may be coupled and twisted to form a single thread, which may be infused with different flavors and colorants, and coated with a protective and binding wax. Several of these threads may be combined to form a floss element. Different monofilament sizes, counts, number and material may be used for the thread, which can have diverse properties and different functions. If the number of monofilaments is increased, the thread strength may be increased, but its elasticity may be decreased. A larger number of monofilaments may increase the diameter of the floss, which may result in a greater risk of damaging the gums due to the difficulty in the dental floss reaching between the tighter spacing between the teeth. If the floss is too thin, it tears and does not provide adequate cleaning capabilities.

Although there have been some improvements in floss designs that permit a thinner floss to expand during use, there is still room for an improved dental floss that has excellent mechanical and physical properties in varying oral mouth conditions and will pass through any tight spacing that may exist between some teeth. An improved floss preferably will provide antioxidant, antimicrobial, and anti-inflammatory results during flossing. A desired floss should also maintain a diameter that does not expand excessively during use to become too bulky for most normal flossing.

SUMMARY OF THE INVENTION

An expandable dental floss may comprise a plurality of texturized threads twisted together forming a floss element. Each thread may comprise a plurality of pre-oriented yarn (POY) filaments. A first set of the plurality of texturized threads may have their POY filaments infused with *Nigella sativa*. A second set of the plurality of texturized threads may have their POY filaments infused with an antiseptic composition.

The first set of the plurality of threads may be a first color and the second set of the plurality of threads may be a second color. Each texturized thread in first and second sets of the plurality of texturized threads may comprise between about 28 and 67 POY filaments. The first and second sets of the plurality of texturized threads may be twisted together at a density of about 60 to 120 twists per meter. The floss element may have a linear mass density value in the range of about 1, 100 to 1, 500 dtex. The POY filaments may comprise polyester filaments.

The antiseptic composition may comprise *Eucalyptus*. The floss element may comprise about 10 to 20 texturized threads twisted together. About 5 to 10 texturized threads from the first set may be twisted with about 5 to 10 texturized threads from the second set. The floss element may comprise about 350 to 700 texturized, POY filaments formed from the first and second sets. The *Nigella sativa* may comprise a supercritical $CO_2$ derived *Nigella sativa* seed oil extract having a thymoquinone concentration of about 27% w/w to 57% w/w of the seed oil extract. The floss element may be free of any binding agent.

In another aspect, a method of manufacturing an expandable dental floss may comprise infusing a plurality of polyester extruded and pre-oriented yarn (POY) filaments with *Nigella sativa* and assembling the *Nigella sativa* infused polyester POY filaments into a thread and texturizing them to form a *Nigella sativa* infused, texturized polyester thread. The method includes infusing a plurality of polyester extruded and pre-oriented yarn (POY) filaments with an antiseptic and assembling the antiseptic infused polyester POY filaments into a thread and texturizing to form an antiseptic infused, texturized polyester thread. The method also includes twisting together at a density of about 60 to 120 twists per meter a first set of about 5 to 10 *Nigella sativa* infused, texturized polyester threads and a second set of about 5 to 10 antiseptic infused, texturized polyester threads together to form a floss element without a binder.

The method may comprise dope dyeing a first color dye into the polyester that is extruded with the *Nigella sativa* and dope dyeing a second color dye into the polyester that is extruded with the antiseptic. The method may comprise infusing the *Nigella sativa* after extruding the plurality of polyester filaments through a spinneret. The method may also comprise infusing the antiseptic after extruding the plurality of polyester filaments through a spinneret.

BRIEF DESCRIPTION OF THE DRAWINGS

Other objects, features and advantages of the present invention will become apparent from the Detailed Description of the invention which follows, when considered in light of the accompanying drawings in which.

DETAILED DESCRIPTION

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

Figure 1:
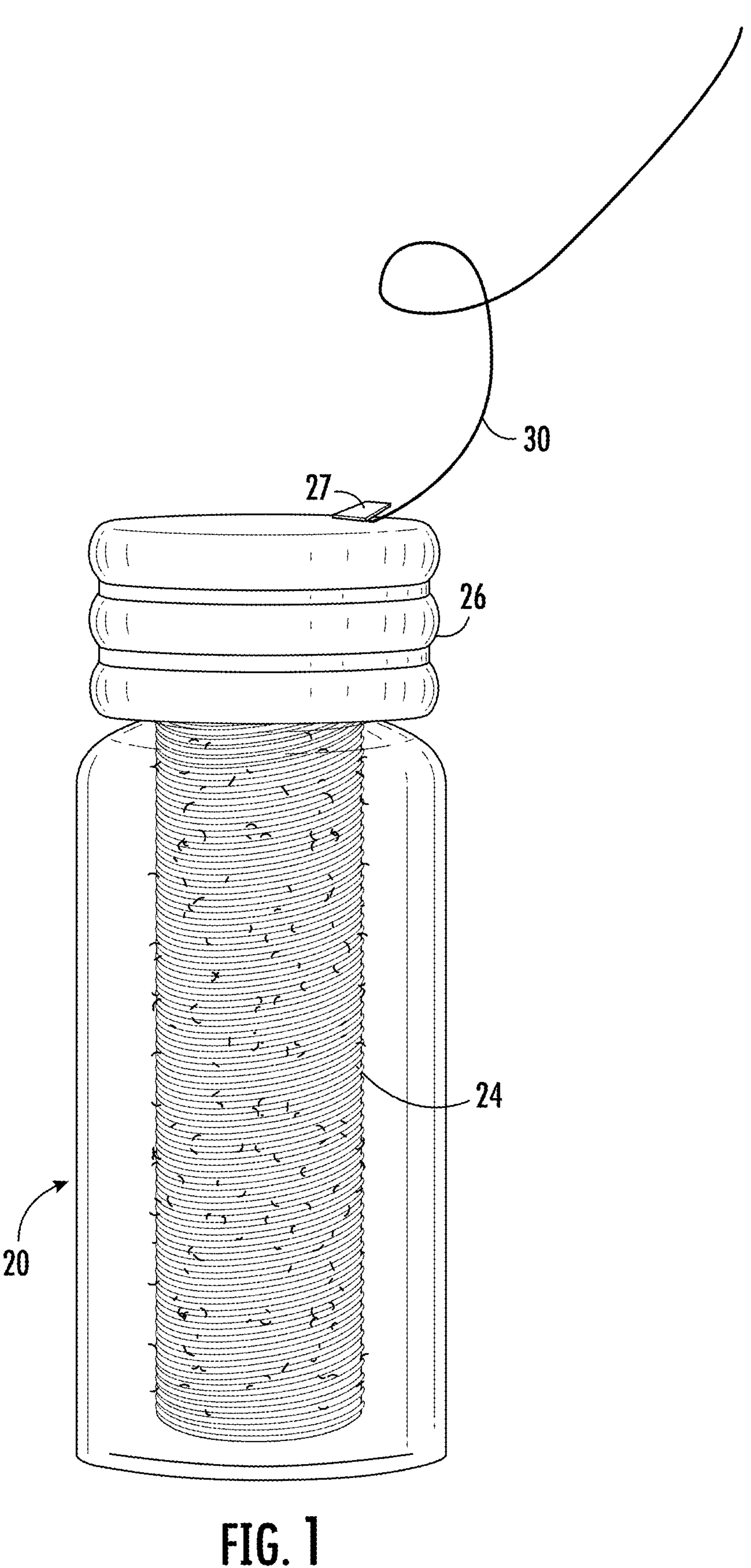
FIG. 1 is a perspective view of a glass jar container containing the expandable dental floss according to the invention.

Referring now to FIG. 1, a glass jar container 20 formed similar to a tube and containing a cylindrical spool 24 of the expandable dental floss 30 is illustrated. A removable cap 26 is screwed on the container 20 and carries a floss cutter 27. The floss 30 is pulled through an opening in the cap 26. The floss bobbin may also be a roll type and the container could be the illustrated glass jar container 20 or a clam shell type construction. As shown in the enlarged but not to scale view of the expandable dental floss 30 of FIG. 2, it includes a plurality of texturized threads 34 that are twisted together forming a floss element 38, which when spooled or separate without spooling, forms the dental floss 30. Each texturized thread 34 is formed from a plurality of pre-oriented yarn (POY) filaments 40, which in this example are formed from polyester filaments. A first set 44 of this plurality of texturized threads 34 have their POY filaments 40 infused with *Nigella sativa*. A second set 46 of the plurality of texturized threads 34 have their POY filaments 40 infused with an antiseptic composition, such as in this example, *Eucalyptus*. Other antiseptic compositions may be used as explained in greater detail below.

Figure 2:
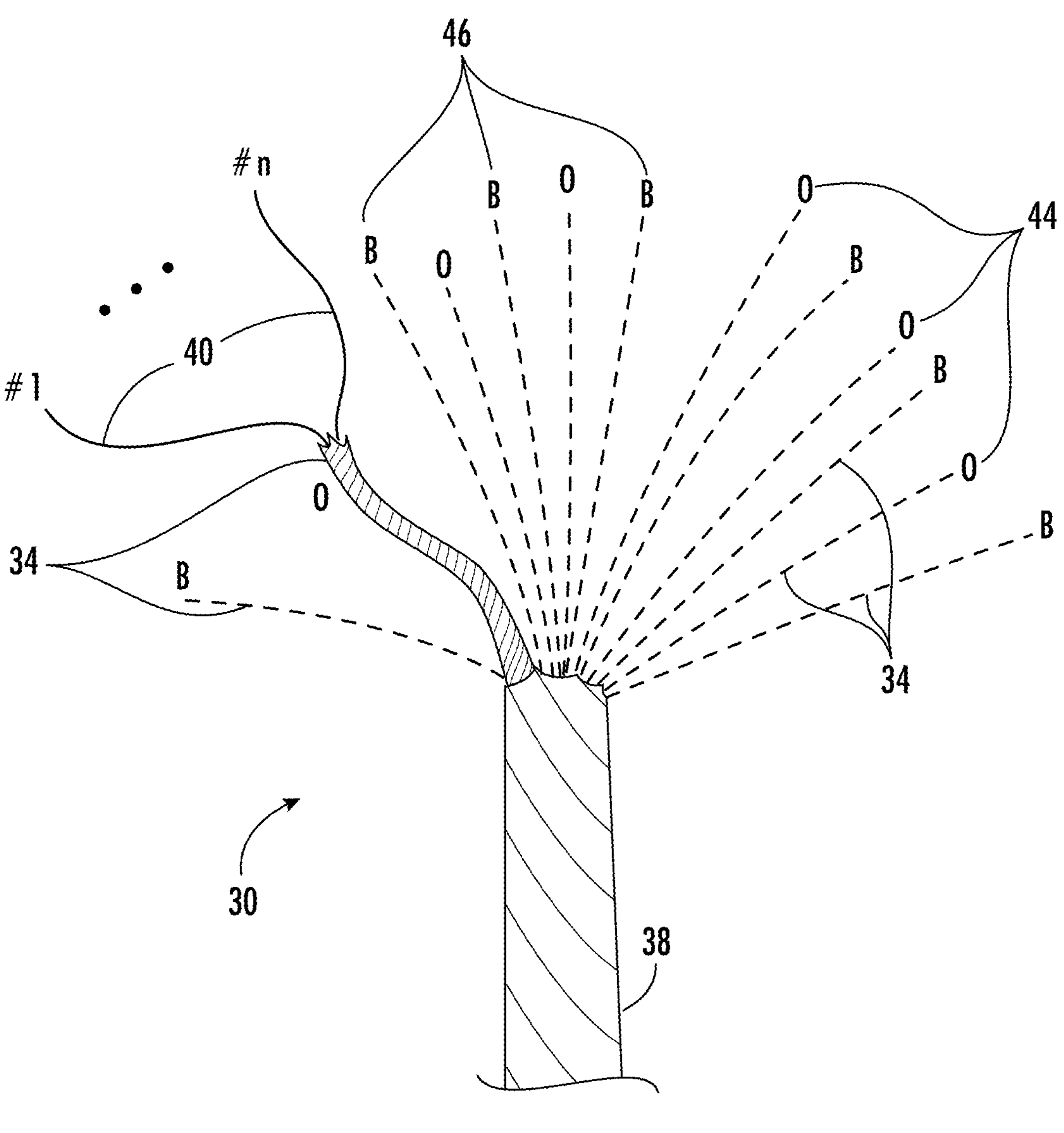
FIG. 2 is an enlarged view of the expandable dental floss of FIG. 1.

The first set 44 of the plurality of texturized threads 34 that is infused with the *Nigella sativa* may be a first color, such as orange (shown by the "O", and the second set 46 of the plurality of texturized threads 34 infused with the antiseptic composition may be a second color, such as black, shown by the "B" in FIG. 2. Each texturized thread 34 may be formed to have between about 28 and 67 polyester POY filaments 40 and in another example between 12 and 60 POY filaments, with the plurality represented by "n" and shown as a first polyester POY filament labeled number one (1) and the last polyester POY filament labeled number "n" in FIG. 2. This range in the number of POY filaments 40 may vary depending on final configuration of the expandable dental floss 30. For example, the threads 34 could each range individually in the number of POY filaments 40 with some threads having as few as 12-15 filaments, and another thread having 28-40 or 40-60 POY filaments or some other range.

The plurality of texturized threads 34 in each of the first and second sets 44,46 may be twisted at a density of about 60 to 120 twists per meter, but may vary to make the floss element 38 compact but not too rigid, but able to expand on bulk. It could be 90 to 110 twists. An example twisting value for the floss element is 100 twists per meter, but could be 90 or 110 twists or a range therebetween. The floss element 38 may have a linear mass density value in the range of about 1,100 to 1, 500 dtex, or 1,000 to 1, 600 dtex in another example to allow the expandable dental floss to penetrate between the teeth, but also to provide mass and bulk to remove food particles and some plaque on both sides of a tooth, which may help prevent further plaque formation. In an example, the floss element 38 may have a 1,370 dtex, which has been found suitable for most flossing applications. The polyester POY filaments 40 are preferred to use for the expandable floss 30, but it may be possible to use other filaments such as nylon, Teflon (PTFE), or polyamide filaments in combination with the polyester filaments, depending upon the type of texturizing that may be required in the thread 34 formation or other function the floss element 38 may include.

The floss element 38 as part of the final expandable dental floss 30 may have about 10 to 20 texturized threads 34 twisted together. This number and range of texturized threads 34 have been found suitable for most dental flossing applications. In an example, about 5 to 10 texturized threads 34 from the first set 44 are twisted with about 5 to 10 texturized threads from the second set 46. Each floss element 38 as the combined and twisted threads 34 may include about 350 to 700 polyester POY filaments 40 depending on their size. This range may vary depending on the final configuration and function desired for the expandable dental floss 30. It may be possible to have as low as 250 total threads depending on the size of the filament. The expandable dental floss 30 includes the bicolor design for the threads 34, featuring in an example black (the antiseptic) and orange (the *Nigella sativa*), which is aesthetically pleasing and practical for many users, aiding users in ensuring a thorough cleaning of their teeth during flossing.

In an example, the *Nigella sativa* that is infused into POY filaments 40 and/or texturized threads 34 is formed from a supercritical $CO_2$ derived *Nigella sativa* seed oil extract having a thymoquinone concentration of about 27% w/w to 57% w/w of the seed oil extract. The expandable dental floss 30 incorporates *Nigella sativa* within its polyester filaments 40 forming the first set of texturized threads 34. The *Nigella sativa* is a potent herb renowned for its benefits in enhancing periodontal health. The active constituent of *Nigella sativa*, thymoquinone, has oral health benefits, making the infusion of the supercritical $CO_2$ derived extract in this expandable dental floss 30 beneficial.

The infusion of *Nigella sativa* into the first set 44 of polyester POY filaments 40 may be accomplished by treating the polyester POY filaments prior to the "weaving" or "interlacing" process. For example, this may be accomplished by infusing the *Nigella sativa* into POY filaments 40 with a vacuum process or by dipping into a solution containing the extract after extruding the plurality of polyester POY filaments through a spinneret, such as during "cool down" as explained in further detail below. The antiseptic composition may be infused within the second set 46 of POY filaments 40 in a similar process. This methodological approach ensures that the active compounds of *Nigella sativa* infused into the dental floss 30 reach the crucial interproximal spaces and gingival sulcus efficiently, targeting areas often overlooked or inadequately cleaned by conventional floss. By doing so, the expandable dental floss 30 may deliver the active compounds, including the *Nigella sativa* and antiseptic composition, where they are needed most, thus elevating the standard of interdental cleaning and promoting better periodontal health.

The expandable dental floss 30 has a meticulous production process, and preferably incorporates a bicolor floss element 38 having a range of about 1,100 to 1,500 dtex, coupled with the *Nigella sativa* and *Eucalyptus* on the respective first and second sets 44,46 of the POY filaments 40 and plurality of texturized threads 34, and a twisting specification of about 100S in an example. This expandable dental floss 30 produced from polyester POY filaments 40 expands between the teeth due to mechanical action. This high performance dental floss 30 works even in cases of xerostomia, i.e., dry mouth.

This coreless design for the dental floss 30 eliminates the need for unnecessary material, enhancing the sustainability efforts of the expandable dental floss. Each of these technical aspects is carefully calibrated to ensure that the expandable dental floss 30 not only meets the functional demands of effective interdental cleaning, but does so with a user-friendly and environmentally conscious design.

The polyester pre-oriented yarn (POY) filaments 40 may have different textures as the physical appearance using different techniques, including stretching partially to form partially oriented filaments and/or bulking where the polyester POY filaments are partially stretched and coupled together to form the thread 34, which may then be twisted, heat set and untwisted, or crimped to texturize. The use of texturized threads 34 that are combined takes advantage of the physical nature and parameters of the polyester and sets the texturized features of the threads in place. The POY filaments 40 and threads 34 after twisting may be entangled mechanically to give body and limit bulkiness. A positive aspect of the dental floss 30 is the correct body may be maintained without chemical agents such as a binder.

A wax coating may be formed on the dental floss 30, such as on the floss element 38 and/or each texturized thread 34, and formed as a microcrystalline or natural wax that may account for about 2% to about 10% of the weight. It may be applied to the expandable dental floss 30 by drawing the floss element 38 through a hot wax mixture, which may be a microcrystalline wax or a blanched natural beeswax in non-limiting examples. In an example, the expandable dental floss 30 is wound, such as on a bobbin, and stored in a glass jar 20 where the glass jar is refillable. Refill bobbins of dental floss 30 and/or jars 20 or containers may be commercially sold with a bobbin of floss that threads into the glass jar container as shown in FIG. 1.

In an example, a final number of 350 to 700 polyester POY filaments 40 may be used to form the floss element 38 as a bulk product from the twisted, texturized threads 34 with a range in the number and/or size of polyester POY filaments to provide sufficient elasticity and avoid gum traumas and display good capability to remove food particles, plaque and impurities. The polyester POY filaments 40 have a low hydroscopic value and are not subject to major structural or form changes, even after prolonged exposure to saliva.

The infused *Nigella sativa* may be formed as the supercritical $CO_2$ extract and includes a greater extracted amount of thymoquinone as in many liquid solvent extracts of *Nigella sativa* and may be added to the polyester POY filaments 40 before twisting, such as after extrusion through spinnerets. The *Nigella sativa* is often referred to as black curcumin, black cumin or black seed. It is a flowering plant native to south and southwest Asia. Various solvents and solvent extraction techniques may be used to extract the active ingredients such as thymoquinone, but in this example, the supercritical $CO_2$ extraction technique using multiple extraction stages is preferred in an example. Other components as ingredients and extracts may be extracted from the plant, such as lipophilic carriers and essential oils.

In an example, the final supercritical $CO_2$ extract of the *Nigella sativa* may be formed from a series of seed processing supercritical $CO_2$ processing stages. The seed of *Nigella sativa* may be ground and sieved to a fine powder of about 20 to 30 mesh. The processed seed may be subject to supercritical $CO_2$ processing at about 120 bar to about 160 bar at about 40° C. to 60° C. for about 25 to 35 minutes and the first fraction collected.

The supercritical $CO_2$ extraction may continue at the same or slightly modified pressure and similar temperatures for a longer period, such as 100 to 140 minutes for the second fractionation compared to the 25 to 35 minutes of the first fractionation, and the second fraction as the extract collected. Pressure may be increased to about 280 to about 320 bar at an increased temperature of about 50° C. to about 70° C. for about 150 to 210 minutes for a third fractionation, and the third extract as a fractionation collected. This fraction and extract may be mixed with other fractions from the process or with the *Nigella sativa* seed or with extracted, spent seeds. Thus, the final extract is a *Nigella sativa* seed oil extract having in one example a thymoquinone concentration of about 27% w/w to 57% w/w of the seed oil extract. Other supercritical $CO_2$ extraction processing parameters may be used to form the supercritical $CO_2$ derived *Nigella sativa* seed oil extract and may range in thymoquinone concentration.

An antiseptic composition in an example is *Eucalyptus* or oil derived from *Eucalyptus* is applied to the second set 46 of plurality of texturized threads 34, such as by infusing the filaments after extrusion, and in an example, before the partial stretching to form the POY filaments 40 and before twisting the threads 34. The *Eucalyptus* operates as a powerful antiseptic. *Eucalyptus* oil may be derived by steam distillation where steam is passed through the leaves causing the essential oils to be released. The steam and oil may be condensed and the oil collected. Other techniques may be used. Besides the *Eucalyptus* as the antiseptic composition, other antiseptic compositions may be used, such as clove oil or a chitosan coating that may include mesoporous bioactive glass nanoparticles. This nanoparticle coating may be applied by dip coating or passing through a solution containing the nanoparticles. Other bioactive nanocomplexes may be incorporated on the dental floss 30 such as chlorhexidine gluconate loaded nanofloss.

Figure 3:
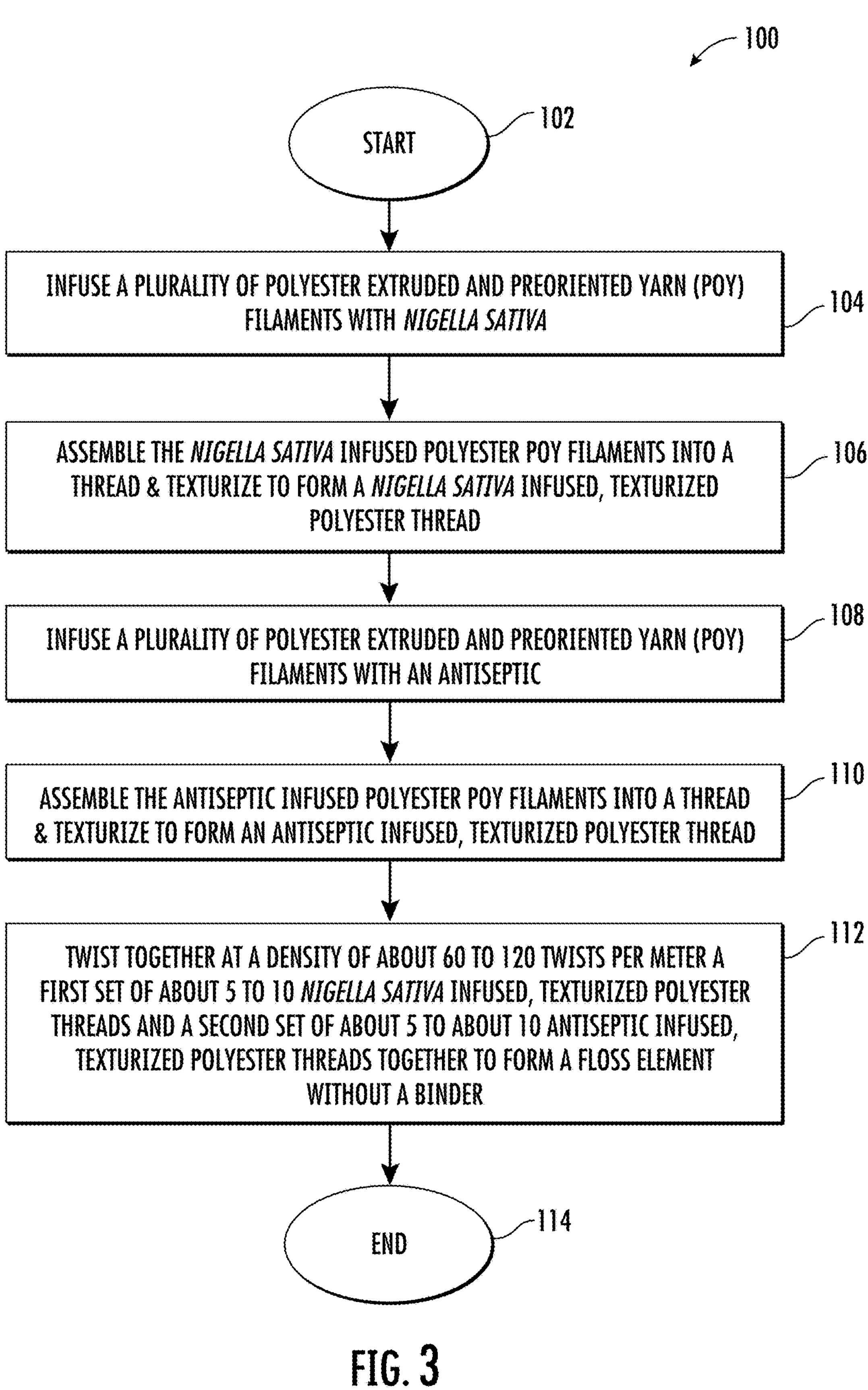
FIG. 3 is a high-level flowchart of an example method of making the expandable dental floss.

Referring now to FIG. 3, there is illustrated generally at 100 a high-level flowchart of the method of manufacturing the expandable dental floss 30 as shown in FIGS. 1 and 2. The process starts (Block 102) and a first set 44 of plurality of polyester, extruded and pre-oriented yarn (POY) filaments 40 are infused with *Nigella sativa* (Block 104). It is possible to infuse the *Nigella sativa* during the cool down and/or partial stretching by vacuum or dipping. The infused polyester POY filaments 40 are assembled into a thread 34 and texturized to form the *Nigella sativa* infused, texturized polyester thread (Block 106).

The process continues by infusing a second set 46 of a plurality of polyester extruded and pre-oriented yarn (POY) filaments 40 with an antiseptic, such as the *Eucalyptus* (Block 108) and assembling the second set 46 of the antiseptic infused polyester POY filaments 40 into a thread 34 and texturizing to form the antiseptic infused, texturized polyester thread (Block 110).

The process further continues by twisting together at a density of about 60 to 120 twists per meter a first set 44 of about 5 to 10 *Nigella sativa* infused, texturized polyester threads 34 and a second set 46 of about 5 to 10 antiseptic infused, texturized polyester threads 34 to form a floss element 38 without a binder (Block 112). Binders often are not adequate in function since upon dissolving with saliva contact, which may vary with each individual, the floss functions differently than intended. Thus, there are no binders, agglomerators, or strengthening agents and by choice of material and processing, the dental floss is expandable but maintains sufficient body for flossing. The process ends (Block 114).

A plurality of these texturized threads 34 form the first set 44 of texturized threads having their POY filaments 40 infused with the *Nigella sativa*. This first set 44 is a first color, such as orange, which may be imparted after the texturized threads 34 are formed or by dope dyeing, also known as solution dying, where the polyester resin may have added color pigment, e.g., the orange pigment, and added, for example, to a polymer paste within a tube. An extrusion screw pushes the colored polymer mixture in this case the orange color, through a small opening or spinneret forming one or more thin filaments. This is advantageous over traditional dyeing processes that are water intensive. The color may also be added to the formed threads 34, usually before texturizing, but may be applied later.

A similar process may be used to form the second set 46 of the plurality of texturized threads 34 having their POY filaments 40 infused with an antiseptic composition by infusing a plurality of polyester extruded and pre-oriented yarn (POY) filaments 40 with an antiseptic and assembling the antiseptic infused polyester POY filaments into a thread 34 and texturizing to form an antiseptic infused, texturized polyester thread.

In both examples, the *Nigella sativa* or antiseptic may be applied after the filaments 40 are extruded, and the filaments have cooled sufficiently so that some vacuum infusion or coating may occur using a gas, or gas and liquid mixture of the *Nigella sativa*. Another production line may be used in a similar process for the antiseptic. The *Nigella sativa* may be formed as a supercritical $CO_2$ oil extract as noted above. The POY filaments 40 of specific color may be passed through a container, holding vessel, or dipping vessel containing the oil extract from *Nigella sativa* or the antiseptic such as *Eucalyptus*.

After the filaments 40 are cooled, they may be stretched partially, or "oriented" to achieve the desired properties of a "partially oriented" filament 40 and then combined or assembled to form the desired thread 34. This thread 34 is then texturized where the assembled filaments forming the fiber may be modified to change their texture and may include bulking with twisting, heat setting and untwisting, or crimping and coiling and other techniques. In an example, about 5 to 10 texturized threads 34 of a first set 44 that are infused with the *Nigella sativa*, and about 5 to 10 threads of a second set 46 that are infused with the antiseptic, such as *Eucalyptus*, are twisted together at a density of about 60 to 120 twists per meter to form the floss element 38. No binder is used as explained above. The direction of the twisting may be in the "S" direction in this example, indicative that when the floss element is held in a vertical position, the visible spirals or helices around its central axis to form in directional slope to the central portion of the letter "S." The individual threads 34 of either first or second sets 44,46 may be twisted in a reverse direction. Also, different threads 34 in either first or second sets 44,46 could be twisted in alternate directions.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

The invention claimed is:

1. An expandable, bicolored, dental floss, comprising;

a plurality of texturized floss threads forming a first set of texturized floss threads, each texturized floss thread in the first set comprising between about 28 and 67 extruded dental floss filaments heat twisted together at a density between about 60 to 120 twists per meter, each texturized floss thread in the first set having a different number of dental floss filaments and twist density from each other, some filaments in each texturized floss thread being partially stretched differently from each other, and each floss filament having a first extrusion infused color and extrusion infused, supercritical $CO_2$ derived *Nigella sativa* seed oil extract with a thymoquinone concentration of about 27% w/w to 57% w/w of the seed oil extract;

a plurality of texturized floss threads forming a second set of texturized floss threads, each texturized floss thread in the second set comprising between about 28 and 67 extruded dental floss filaments heat twisted together at a density between about 60 to 120 twists per meter, each texturized floss thread in the second set having a different number of dental floss filaments and twist density from each other, some filaments in each texturized floss thread being partially stretched differently from each other, and each floss filament having a second extrusion infused color and an extrusion infused antiseptic composition; and each of the first and second sets of texturized floss threads twisted together in alternating "S" and reverse directions and having a total linear mass density value in the range of about 1,100 to 1,500 dtex and a total number of 350 to 700 filaments from the first and second sets.

2. The dental floss of claim 1 wherein the first set of the plurality of texturized floss threads is orange and the second set of the plurality of texturized floss threads is black.

3. The dental floss of claim 1 wherein at least one texturized floss thread in first and second sets of the plurality of texturized floss threads comprises between about 28 and 40 dental floss filaments.

4. The dental floss of claim 1 wherein at least one of said first and second sets of the plurality of texturized floss threads are twisted together at a density of about 90 to 110 twists per meter.

5. The dental floss of claim 1 wherein the linear mass density value is about 1, 370 dtex.

6. The dental floss of claim 1 wherein said dental floss filaments comprise polyester filaments.

7. The dental floss of claim 1 wherein the antiseptic composition comprises *Eucalyptus*.

8. The dental floss of claim 1 wherein about 10 to 20 texturized floss threads from first and second sets are twisted together.

9. The dental floss of claim 8 wherein about 5 to 10 texturized floss threads from the first set are twisted with about 5 to 10 texturized floss threads from the second set.

10. The dental floss of claim 1 wherein the dental floss comprises about 350 to 700 dental floss filaments formed from the first and second sets.

11. The dental floss of claim 1 wherein each texturized floss thread is free of any binding agent.

* * * * *